(12) United States Patent
Ghebremeskel et al.

(10) Patent No.: US 8,715,713 B2
(45) Date of Patent: May 6, 2014

(54) SOLVENT CAST FILM SUSTAINED RELEASE LATANOPROST IMPLANT

(75) Inventors: Alazar N. Ghebremeskel, Irvine, CA (US); Lon T. Spada, Walnut, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/457,785

(22) Filed: Apr. 27, 2012

(65) Prior Publication Data

US 2012/0276184 A1 Nov. 1, 2012

Related U.S. Application Data

(60) Provisional application No. 61/480,657, filed on Apr. 29, 2011, provisional application No. 61/480,630, filed on Apr. 29, 2011.

(51) Int. Cl.
*A61F 2/00* (2006.01)
*A61K 9/00* (2006.01)
*A61F 9/00* (2006.01)
*A61K 31/5575* (2006.01)
*A61K 47/34* (2006.01)

(52) U.S. Cl.
CPC ............ *A61K 9/0051* (2013.01); *A61F 9/0017* (2013.01); *A61K 31/5575* (2013.01); *A61K 47/34* (2013.01)
USPC .......................................... 424/428; 514/530

(58) Field of Classification Search
None
See application file for complete search history.

(56) References Cited

U.S. PATENT DOCUMENTS

| | | | |
|---|---|---|---|
| 5,296,504 | A | 3/1994 | Stjernschantz et al. |
| 5,422,368 | A | 6/1995 | Stjernschantz et al. |
| 5,578,618 | A | 11/1996 | Stjernschantz et al. |
| 5,627,208 | A | 5/1997 | Stjernschantz et al. |
| 5,660,854 | A | 8/1997 | Haynes et al. |
| 5,830,139 | A | 11/1998 | Abreu et al. |
| 5,849,791 | A | 12/1998 | Stjernschantz et al. |
| 6,030,999 | A | 2/2000 | Stjernschantz et al. |
| 6,120,460 | A | 9/2000 | Abreu et al. |
| 6,187,813 | B1 | 2/2001 | Stjernschantz et al. |
| 6,312,393 | B1 | 11/2001 | Abreu et al. |

(Continued)

FOREIGN PATENT DOCUMENTS

| | | |
|---|---|---|
| EP | 1944032 | 7/2008 |
| EP | 2004172 | 12/2008 |

(Continued)

OTHER PUBLICATIONS

Aihara et al, "Enhanced FGF-2 movement through human sclera after exposure to latanoprost", Invest Ophthalmol Vis Sci., 42(11); 2554-9, 2001.

(Continued)

*Primary Examiner* — Bethany Barham
(74) *Attorney, Agent, or Firm* — Jennifer C. Cheng; Joel B. German; Debra D. Condino

(57) ABSTRACT

The present invention provides a sustained release latanoprost implant in the form of a thin film comprising latanoprost incorporated in a biodegradable polymer matrix. Preferably, said implant is an intraocular implant comprising a thin film comprising latanoprost incorporated in a biodegradable polymer matrix wherein said implant is configured as a disc or a rolled film that can be inserted into the eye and unrolls to provide a film having a high surface area to volume ratio.

4 Claims, 2 Drawing Sheets

(56) References Cited

U.S. PATENT DOCUMENTS

| | | | |
|---|---|---|---|
| 6,395,787 B1 | 5/2002 | Woodward et al. |
| 6,403,649 B1 | 6/2002 | Woodward et al. |
| 6,417,230 B2 | 7/2002 | Stjernschantz et al. |
| 6,429,226 B1 | 8/2002 | Stjernschantz et al. |
| 6,544,193 B2 | 4/2003 | Abreu et al. |
| 7,041,063 B2 | 5/2006 | Abreu et al. |
| 7,143,709 B2 | 12/2006 | Brennan et al. |
| 7,226,455 B2 | 6/2007 | Jeannin et al. |
| 7,403,805 B2 | 7/2008 | Abreu et al. |
| 7,514,474 B1 | 4/2009 | Lubit et al. |
| 7,517,912 B1 | 4/2009 | Lubit et al. |
| 7,541,382 B2 | 6/2009 | Lubit et al. |
| 7,550,508 B2 | 6/2009 | Lubit et al. |
| 7,553,874 B2 | 6/2009 | Lubit et al. |
| 7,553,875 B2 | 6/2009 | Lubit et al. |
| 7,589,057 B2 | 9/2009 | Hughes et al. |
| 7,632,867 B2 | 12/2009 | Lubit et al. |
| 7,632,868 B2 | 12/2009 | Lubit et al. |
| 7,635,720 B2 | 12/2009 | Lubit et al. |
| 7,638,557 B2 | 12/2009 | Lubit et al. |
| 7,645,800 B2 | 1/2010 | Lubit et al. |
| 7,649,021 B2 | 1/2010 | Lubit et al. |
| 7,650,848 B2 | 1/2010 | Brennan et al. |
| 7,654,957 B2 | 2/2010 | Abreu |
| 7,756,559 B2 | 7/2010 | Abreu et al. |
| 7,799,336 B2 | 9/2010 | Hughes et al. |
| 7,809,417 B2 | 10/2010 | Abreu et al. |
| 7,837,801 B2 | 11/2010 | Christopher et al. |
| 7,993,634 B2 | 8/2011 | Hughes et al. |
| 8,119,154 B2 | 2/2012 | Huang et al. |
| 8,147,865 B2 | 4/2012 | Huang et al. |
| 8,206,736 B2 | 6/2012 | Hughes et al. |
| 8,206,737 B2 | 6/2012 | Hughes et al. |
| 8,445,027 B2 | 5/2013 | Hughes et al. |
| 2002/0035264 A1 | 3/2002 | Kararli et al. |
| 2002/0049389 A1 | 4/2002 | Abreu et al. |
| 2003/0139687 A1 | 7/2003 | Abreu et al. |
| 2004/0039297 A1 | 2/2004 | Abreu et al. |
| 2004/0039298 A1 | 2/2004 | Abreu et al. |
| 2005/0244464 A1 | 11/2005 | Hughes et al. |
| 2005/0244468 A1 | 11/2005 | Huang et al. |
| 2005/0244469 A1 | 11/2005 | Whitcup et al. |
| 2005/0244474 A1 | 11/2005 | Huang et al. |
| 2006/0141049 A1 | 6/2006 | Lyons et al. |
| 2006/0173060 A1 | 8/2006 | Hughes et al. |
| 2006/0182781 A1 | 8/2006 | Hughes et al. |
| 2006/0246145 A1 | 11/2006 | Hughes et al. |
| 2006/0292099 A1 | 12/2006 | Milburn et al. |
| 2007/0014833 A1 | 1/2007 | Milburn et al. |
| 2007/0016074 A1 | 1/2007 | Abreu et al. |
| 2007/0031472 A1 | 2/2007 | Huang et al. |
| 2007/0142718 A1 | 6/2007 | Abreu |
| 2007/0190111 A1 | 8/2007 | Robinson et al. |
| 2007/0224246 A1 | 9/2007 | Hughes et al. |
| 2007/0243230 A1 | 10/2007 | De Juan et al. |
| 2007/0260203 A1 | 11/2007 | Donello et al. |
| 2007/0269487 A1 | 11/2007 | De Juan et al. |
| 2007/0287749 A1 | 12/2007 | Sawa et al. |
| 2007/0292476 A1 | 12/2007 | Landis et al. |
| 2008/0038317 A1 | 2/2008 | Chang et al. |
| 2008/0131481 A1 | 6/2008 | Hughes et al. |
| 2008/0131482 A1 | 6/2008 | Hughes et al. |
| 2008/0131484 A1 | 6/2008 | Robinson et al. |
| 2008/0145403 A1 | 6/2008 | Spada et al. |
| 2008/0145407 A1 | 6/2008 | Huang et al. |
| 2008/0152694 A1 | 6/2008 | Lobl et al. |
| 2008/0181930 A1 | 7/2008 | Rodstrom et al. |
| 2009/0081277 A1 | 3/2009 | Robinson et al. |
| 2009/0092654 A1 | 4/2009 | De Juan et al. |
| 2009/0148527 A1 | 6/2009 | Robinson et al. |
| 2009/0280158 A1 | 11/2009 | Butuner |
| 2010/0015158 A1 | 1/2010 | Robinson et al. |
| 2010/0074957 A1 | 3/2010 | Robinson et al. |
| 2010/0104654 A1 | 4/2010 | Robinson et al. |
| 2010/0124565 A1 | 5/2010 | Spada et al. |
| 2010/0145180 A1 | 6/2010 | Abreu |
| 2010/0168250 A1 | 7/2010 | Cruz |
| 2010/0209477 A1 | 8/2010 | Butuner et al. |
| 2010/0209478 A1* | 8/2010 | Sawhney et al. ............ 424/427 |
| 2010/0226943 A1 | 9/2010 | Brennan et al. |
| 2010/0247606 A1 | 9/2010 | Robinson et al. |
| 2010/0278898 A1 | 11/2010 | Hughes et al. |
| 2011/0002866 A1 | 1/2011 | Lubit et al. |
| 2011/0028807 A1 | 2/2011 | Abreu et al. |
| 2011/0040161 A1 | 2/2011 | Abreu |
| 2011/0182966 A1 | 7/2011 | Robinson et al. |
| 2011/0212090 A1 | 9/2011 | Pedersen et al. |
| 2011/0250285 A1 | 10/2011 | Hughes et al. |
| 2011/0276131 A1 | 11/2011 | De Juan et al. |
| 2012/0219611 A1 | 8/2012 | Hughes et al. |
| 2012/0245505 A1 | 9/2012 | Robinson et al. |
| 2012/0276186 A1 | 11/2012 | Ghebremeskel et al. |

FOREIGN PATENT DOCUMENTS

| | | |
|---|---|---|
| EP | 2037881 | 3/2009 |
| EP | 2124879 | 12/2009 |
| EP | 2276492 | 1/2011 |
| EP | 2358349 | 8/2011 |
| EP | 2389221 | 11/2011 |
| EP | 2411013 | 2/2012 |
| WO | WO2005-110424 | 11/2005 |
| WO | WO 2006-031658 | 3/2006 |
| WO | WO 2007-115261 | 10/2007 |
| WO | WO 2008-019198 | 2/2008 |
| WO | WO 2008-070402 | 6/2008 |
| WO | WO 2008-079674 | 7/2008 |
| WO | WO 2009/035562 | 3/2009 |
| WO | WO 2009-129187 | 10/2009 |
| WO | WO 2009-137085 | 11/2009 |
| WO | WO-2009-143288 | 11/2009 |
| WO | WO2010-056598 | 5/2010 |
| WO | WO 2010-062523 | 6/2010 |
| WO | WO 2010/062523 | 6/2010 |
| WO | WO 2010-085696 | 7/2010 |
| WO | WO 2010-011449 | 9/2010 |
| WO | WO 2010135369 A1 * | 11/2010 |
| WO | WO2011-075481 | 6/2011 |
| WO | WO 2011-091205 | 7/2011 |
| WO | WO 2011-127064 | 10/2011 |
| WO | WO 2011-130462 | 10/2011 |
| WO | WO 2012-021108 | 2/2012 |

OTHER PUBLICATIONS

Goldstein et al, "Intraocular pressure in patients with uveitis treated with fluocinolone acetonide implants", Archives of Ophthalmology, 125(11), 1478-1485, 2007.

Heller, Biodegradable Polymers in Controlled Drug Delivery, In: CRC Critical Reviews in Therapeutic Drug Carrier Systems, vol. 1, CRC Press, Boca Raton, Fla. 1987, pp. 39-90.

Janoria et al, "Novel approaches to retinal drug delivery", Expert Opinion on Drug Delivery, vol. 4, 371-388, Jul. 1, 2007.

Kim et al, "Increased human sclera permeability with prostaglandin exposure", Invest Ophthalmol Vis Sci.; 42(7); 1515-21, 2001.

Mansouri et al, "Quality of diurnal intraocular pressure control in open-angle patients treated with latanoprost compared surgically treated glaucoma patients: a prospective", The British Journal of Ophthalmology, vol. 92, No. 3, pp. 332-336, Mar. 2008.

Marquis et al, "Management of glaucoma: Focus on pharmacological therapy", Drugs and Aging, vol. 22, No. 1, 1-21, 2005.

Woodward et al, "Identification of an antagonist that selectively blocks the activity of prostamides (prostaglandin-ethanolamides) in the feline iris", British Journal of Pharmacology, 150, 342-352, 2007.

Woodward et al, "Fixed-combination and emergin glaucoma therapies", Expert Opinion on Emerging Drugs, vol. 12, No. 2, 313-327, May 1, 2007.

Xalatan®, latanoprost ophthalmic solution. Product Information:Pharmacia & Upjohn Company, Kalamazoo, MI, Dec. 2, 2010, 3 pages.

U.S. Appl. No. 10/837,260, Hughes et al, filed Apr. 30, 2004.

(56) References Cited

OTHER PUBLICATIONS

Alimera, "Psivida: Small-Cap Ophthalmology-Based BioTech Positioned for Long-Term Growth", LexisNexis by Comtex News Network, Inc., Thomson Reuters ONE, Jun. 27, 2012, 2 pages.
Merkli et al, Use of Insoluble Biodegradable Polymers in Ophthalmic Systems for the Sustained Release of Drugs, European Journal of Pharmaceutics and Biopharmaceutics, vol. 41, No. 5, Oct. 1, 1995, pp. 271-283.
International Search Report, PCT/US2012/035411, Date of Mailing Sep. 17, 2012, Allergan, Inc.
U.S. Appl. No. 12/259,153, filed Oct. 27, 2008.
U.S. Appl. No. 13/457,813, filed Apr. 27, 2012.
U.S. Appl. No. 13/596,904, filed Aug. 28, 2012.
Kivalo et al. (1999) "Biodegradable tube implants in experimental glaucoma surgery in the rabbit" *J. Materials Science: Materials in Medicine* 10:53-58.

* cited by examiner

SOLVENT CAST FILM SUSTAINED RELEASE LATANOPROST IMPLANT

CROSS REFERENCE TO RELATED APPLICATIONS

This application claims the benefit of U.S. Provisional Application No. 61/480,657, filed Apr. 29, 2011, and U.S. Provisional Application 61/480,630, filed Apr. 29, 2011. The contents of each of these provisional applications are hereby incorporated by reference.

BACKGROUND OF THE INVENTION

1. Field of the Invention

The present invention relates to biodegradable intraocular implants that provide for the sustained release of latanoprost, and to methods of making these implants, and to methods of using these implants to reduce elevated intraocular pressure in individuals in need thereof.

2. Summary of the Related Art

Latanoprost is a prostaglandin $F_{2\alpha}$ analogue which is indicated in the treatment of open-angle glaucoma or ocular hypertension in patients who are intolerant of other intraocular pressure (IOP)—lowering medications or insufficiently responsive (i.e., failed to achieve target IOP after multiple measurements over time) to another IOP-lowering medication. Latanoprost may be used alone or in combination with other antiglaucoma agents.

Latanoprost is an isopropyl ester prodrug. It is hydrolyzed by esterases in the cornea to latanoprost acid, which is biologically active. The elimination of latanoprost acid from plasma is rapid (half-life 17 minutes) after either ophthalmic or intravenous administration. Latanoprost's pharmacology makes it a candidate for formulation as an IOP lowering sustained release polymer implant. However, its physicochemical properties make it an extremely challenging molecule to incorporate into a biodegradable implant. That is, Latanoprost (MW 432.58) is a colorless to slightly yellow oil that is very soluble in acetonitrile and freely soluble in acetone, ethanol, ethyl acetate, isopropanol, methanol and octanol. It is practically insoluble in water. It is believed that a latanoprost sustained release implant would be an effective treatment for long-term reduction of intraocular pressure associated with glaucoma or other ocular diseases.

BRIEF SUMMARY OF THE INVENTION

The present invention provides a sustained release polymer implant containing latanoprost. In this invention, latanoprost is incorporated into a solid biodegradable implant, wherein said implant is in the form of a thin clear-film. The film can be cut to any shape and dimension. One example is a thin disc shaped film that is about 50 µm to about 100 µm thick, or about 100 µm to about 500 µm thick, and about 2 mm to about 6 mm in diameter. In ophthalmic use, the thin film, if it is small enough, may be inserted directly into a region of the eye, or it may be rolled-up and inserted (e.g., through a small opening) into a region of the eye such as the subTenon's space (the virtual space between Tenon's capsule and the sclera). For example, a rolled-up film may be inserted into the sub-Tenon's space using a needle and syringe. Once inserted, it may partially or completely unfurl to its original disc shape providing a large surface for drug diffusion through the sclera.

Tenon's capsule is the thin fibrous elastic membrane that envelops the eyeball from the edge of the cornea (limbus) to the optic nerve. It attaches loosely to the sclera and to the extraocular muscle tendons.

In another embodiment the rolled film can be inserted into the subTenon's space, subconjunctival space, the vitreous body, or the anterior chamber of the eye to treat a patient suffering from elevated intraocular pressure (i.e., ocular hypertension), such as a patient having glaucoma.

Accordingly, one embodiment is a film comprising or consisting of latanoprost and a biodegradable polymer. The latanoprost may be homogenously distributed throughout the biodegradable film.

The film can be configured for use as an intraocular implant, which may provide for the continuous release of latanoprost into the eye for a period of at least about 3 to about 6 months after placement of the implant in the sub-Tenon's space or subconjunctival space of the eye. The release pattern of the implant may be linear or non-linear.

The intraocular implant can be in the form of a flat disc or a rolled film.

The biodegradable polymer can be a hydroxyaliphatic carboxylic acid, a polysaccharide, a poly(D-lactide), a poly(L-lactide), a poly(D,L-lactide), a polyglycolide, a polycaprolactone, or combinations thereof.

The biodegradable polymer can be selected from the group consisting of polyvinyl alcohol, polyesters, polyethers and combinations thereof which are water soluble or biocompatible and may be biodegradable and/or bioerodible.

The polysaccharide may be selected from the group consisting of calcium alginate, and functionalized celluloses.

The functionalized cellulose can be a carboxymethylcellulose ester characterized by being water insoluble and having a molecular weight of about 5 kD to 500 kD.

The biodegradable polymer can be a poly(D-lactide), a poly(L-lactide), a poly(D,L-lactide), a polyglycolide, or a poly(D,L-lactide-co-glycolide) (PLGA), wherein the molar percent of D,L-lactide in the PLGA can be 0-100%, about 15-85%, or about 35-65%. More specifically, the molar ratio of D,L-lactide to glycolide in the PLGA copolymer can be about 50:50, about 75:25, or about 85:15.

For example, the biodegradable polymer can be a 50:50 or 75:25 poly(D,L-lactide-co-glycolide) (PLGA) copolymer.

The biodegradable polymer, whether a PLA or PLGA, may have acid or ester end groups.

Another embodiment is a method of providing latanoprost to a patient in need thereof, the method comprising rolling a film comprising latanoprost and a biodegradable polymer into a cylindrical shape, inserting said rolled film into the eye of the patient, whereby said film can unroll or partially unfurl to provide for drug diffusion out of the film into the eye. In particular embodiments, the rolled film may be inserted into the subTenon's space, subconjunctival space, vitreous body, or anterior chamber of the eye. By unrolling or partially unfurling, the film may thereby expose its entire surface for drug diffusion.

The film can be about 25 µm to about 75 µm thick, or about 25 µm to about 100 µm thick.

The rolled film can be inserted into the subTenon's space of the eye through a small opening and allowed to unfurl to its original shape or to a concentric sheet, thereby providing a large surface for drug diffusion through the sclera.

In some embodiments, the small opening may be less than about 2 mm, or less than about 4 mm.

The patient in need of latanoprost can be a person (i.e., individual) suffering from glaucoma. Accordingly, one embodiment is a method for reducing intraocular pressure (IOP) in the eye of a patient in need thereof, the method comprising rolling a film comprising latanoprost and a biodegradable polymer into a cylindrical shape, and inserting said rolled film into the sub-Tenon's space, subconjunctival space, vitreous body, or anterior chamber of the eye of the patient, whereupon the rolled film partially or completely unrolls or unfurls in the eye thereby providing for diffusion of drug out of the film into the eye.

In one embodiment the intraocular implant comprises 30% w/w latanoprost, 35% w/w RESOMER® 8208, and 35% W/W RESOMER® RG755S.

In another embodiment the intraocular implant comprises 30% w/w latanoprost, 35% w/w RESOMER® 8208, and 35% w/w RESOMER® RG752S.

In another embodiment the intraocular implant comprises 30% w/w latanoprost, 35% w/w RESOMER® 8208, and 35% w/w RESOMER® R203S.

In another embodiment the intraocular implant comprises 30% w/w latanoprost, 35% w/w RESOMER® R203S, and 35% w/w RESOMER® RG755S.

Another embodiment is a biodegradable intraocular implant for reducing intraocular pressure in an eye of an individual in need thereof, the implant comprising latanoprost and a biodegradable polymer, wherein
a) the implant does not contain bimatoprost;
b) the implant is in the form of a disc (e.g., a flat disc) or a rolled film;
c) said film is about 100 μm to about 500 μm thick and about 2 to about 6 mm in diameter;
d) the solubility parameter for each of the latanoprost and biodegradable polymer(s) differ one from the other by no more than 10 MPa$^{1/2}$;
e) the implant releases latanoprost continuously for at least 30 days after placement in the eye of the individual; and wherein
f) said biodegradable polymer is:
   i) an ester terminated poly(D,L-lactide) having an inherent viscosity of about 1.8-2.2 dl/g (R208);
   ii) an ester terminated poly(D,L-lactide) having an inherent viscosity of about 0.25-0.35 dl/g (R203S);
   iii) an ester terminated poly(D,L-lactide-co-glycolide) having an inherent viscosity of about 0.16-0.24 dl/g and a D,L-lactide to glycolide ratio of about 75:25 (RG752S); or
   iv) an ester terminated poly(D,L-lactide-co-glycolide) having an inherent viscosity of about 0.50-0.70 dl/g and a D,L-lactide to glycolide ratio of about 75:25 (RG755S); or
   v) a combination of any two or more of i, ii, iii, or iv.

In another embodiment the biodegradable implant does not contain a prostamide.

One embodiment provides for a biodegradable implant comprising or consisting of about 30% by weight latanoprost, about 35% by weight of an ester terminated poly(D,L-lactide) having an inherent viscosity of about 1.8-2.2 dl/g (R208), and about 35% by weight of an ester terminated poly(D,L-lactide-co-glycolide) having an inherent viscosity of about 0.50-0.70 dl/g and a D,L-lactide:glycolide ratio of about 75:25 (RG755S).

Another embodiment provides for a biodegradable implant comprising or consisting of about 30% by weight latanoprost, about 35% by weight of an ester terminated poly(D,L-lactide) having an inherent viscosity of about 1.8-2.2 dl/g (R208), and about 35% by weight of an ester terminated poly(D,L-lactide) having an inherent viscosity of about 0.25-0.35 dl/g (R203S).

Another embodiment provides for a method of making a biodegradable intraocular implant, the method comprising:
a) combining latanoprost and the biodegradable polymer(s) in a receptacle;
b) mixing the latanoprost and biodegradable polymer(s) in the receptacle using a spatula to form a mixture;
c) transferring the mixture to a glass culture dish:
d) dissolving the dish mixture in a solvent selected from the group consisting of dichloromethane, ethyl acetate, chloroform, acetone, and acetonitrile, to form a solution;
e) casting the solution into a dish;
f) drying the cast for about 24 hours to form a film;
g) cutting the film into circular portions of about 4 mm in diameter;
h) rolling said circular portions to form a rolled film for placement in the eye of an individual in need thereof.

RESOMER® R208 is an ester terminated poly(D,L-lactide) having an inherent viscosity of about 1.8-2.2 dl/g, as measured for a 0.1% solution in chloroform at 25° C.

RESOMER® R202S is an ester terminated poly(D,L-lactide) having an inherent viscosity of about 0.16-0.24 dl/g, as measured for a 0.1% solution in chloroform at 25° C.

RESOMER® R203S is an ester terminated poly(D,L-lactide) having an inherent viscosity of about 0.25-0.35 dl/g, as measured for a 0.1% solution in chloroform at 25° C.

RESOMER® RG752S is an ester terminated poly(D,L-lactide-co-glycolide) having an inherent viscosity of about 0.16-0.24 dl/g (as measured for a 0.1% solution in chloroform at 25° C.), and a D,L-lactide:glycolide ratio of about 75:25.

RESOMER® RG755S is an ester terminated poly(D,L-lactide-co-glycolide) having an inherent viscosity of about 0.50-0.70 dl/g (as measured for a 0.1% solution in chloroform at 25° C.), and a D,L-lactide:glycolide ratio of about 75:25.

Another embodiment is a method for making a biodegradable film, the film comprising or consisting of latanoprost and a biodegradable polymeric matrix, whereby the film is configured for placement in the sub-Tenon space, subconjunctival space, vitreous body, or anterior chamber of the eye, and whereby the film provides for the continuous release of latanoprost over a period of at least about one month, or at least about 3 to about 6 months after placement in the eye, the method comprising dissolving latanoprost and a biodegradable polymer or combination of two or more biodegradable polymers in a solvent to form a solution, sonicating the solution, casting the solution in a receptacle (e.g., a glass dish), and evaporating the solvent to form a biodegradable polymeric film.

Non-limiting examples of organic solvents that can be used to dissolve latanoprost and a biodegradable polymer include dichloromethane, ethyl acetate, chloroform, acetone, and acetonitrile. Other solvents may also be used. The solvent is selected based on its solubility parameter in relation to that of the biodegradable polymer(s) and latanoprost. The solubility parameter of the organic solvent should differ no more than 10 MPa$^{1/2}$ from those of the biodegradable polymer(s) and latanoprost.

DEFINITIONS

"About" means that the number, range, value or parameter so qualified encompasses ten percent more and ten percent less of the number, range, value or parameter.

"Treat", "treating", or "treatment" means a reduction or resolution or prevention of an ocular condition, ocular injury or damage, or to promote healing of injured or damaged ocular tissue. A treatment is usually effective to reduce at least one symptom of an ocular condition, ocular injury or damage.

"Therapeutically effective amount" means the level or amount of agent needed to treat an ocular condition, or reduce a symptom associated with the condition without causing significant negative or adverse side effects to the eye or a region of the eye. In view of the above, a therapeutically effective amount of latanoprost is an amount that is effective in reducing intraocular pressure in an eye of an individual.

"Therapeutic component" means that portion of an implant other than the polymer matrix comprising one therapeutic agent used to treat an ocular condition. The therapeutic component can be a discrete region of an implant, or it may be homogenously distributed throughout the implant.

"Biodegradable polymer" means a polymer or polymers which degrade in vivo, and wherein erosion of the polymer or polymers over time occurs concurrent with or subsequent to release of the therapeutic agent, e.g., the latanoprost. The terms "biodegradable" and "bioerodible" are equivalent and are used interchangeably herein. A biodegradable polymer may be a homopolymer, a copolymer, or a polymer comprising more than two different polymeric units. The polymer can be a gel or hydrogel type polymer. Examples include PLA or PLGA polymers or mixtures or derivatives thereof.

Prostamides (prostaglandin-ethanolamides) have been described by, for example, Woodward et al. (2007) *British Journal of Pharmacology* 150:342-352. Prostamides have been disclosed in, for example, U.S. Pat. Nos. 6,395,787 and 6,403,649.

The solubility parameter for a substance is a numerical value which indicates the relative solvency behavior of that substance. The concept is discussed and defined in US 2008/0145403.

DETAILED DESCRIPTION OF THE INVENTION

Figure 1A:
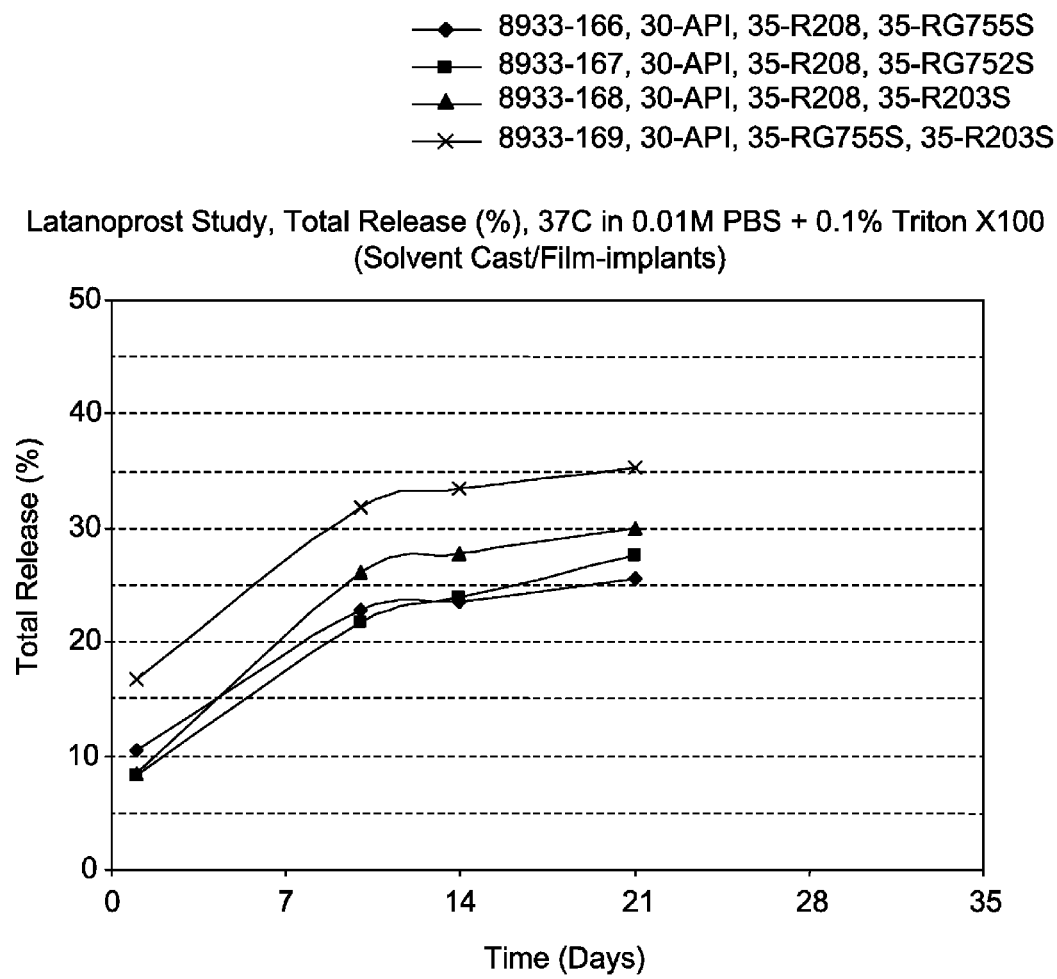
FIGS. 1A and B show release profiles for latanoprost-containing formulations of Example 1.

The present invention provides an implant, e.g. an intraocular implant comprising a thin film of latanoprost in a biodegradable polymer matrix.

Latanoprost is disclosed in U.S. Pat. Nos. 6,429,226; 6,417,230; 6,187,813; 6,030,999; 5,849,791; 5,627,208; 5,578,618; 5,422,368 and 5,296,504 and has the following structure:

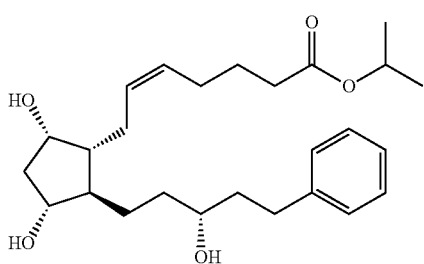 [SMILES: CC(C)OC(=O)CCC/C=C\C[C@@H]1[C@@H](CC[C@@H](O)CCc2ccccc2)[C@H](O)C[C@@H]1O]

In the present invention latanoprost is incorporated into a biodegradable polymer film by dissolving latanoprost in a solvent for latanoprost and the polymer to form a solution of latanoprost and the polymer, casting a film of said solution and removing said solvent to provide said biodegradable polymer film.

The thickness of said film is controlled by adjusting the thickness of said cast solution and/or the solids content of the latanoprost/polymer solution. Preferably said thickness is from about 25 to about 500 μm, e.g. about 25 to about 75 μm, or about 100 μm to about 500 μm thick.

Suitable polymeric materials or compositions for use in the implant include those materials which are compatible, i.e. biocompatible, with the eye so as to cause no substantial interference with the functioning or physiology of the eye. Such materials preferably are at least partially and more preferably substantially completely biodegradable or bioerodible or bioabsorbable.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility, ease of use of the polymer in making the implant of the present invention, a half-life in the physiological environment of at least about 6 hours, preferably greater than about one day, and not significantly increasing the viscosity of the vitreous.

The biodegradable polymeric materials which are included to form the implant are desirably subject to enzymatic or hydrolytic instability. Water-soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 200 kD usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The percent of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of the drug (latanoprost) from an erodible polymer is the consequence of several mechanisms or combinations of mechanisms. Some of these mechanisms include desorption from the implant's surface, dissolution, diffusion through porous channels of the hydrated polymer and erosion. Erosion can be bulk or surface or a combination of both. The shell of the intraocular implant may release drug at a rate effective to sustain release of an amount of drug for more than one week after implantation into an eye. In certain implants, therapeutic amounts of drug are released for no more than about 30-35 days after implantation. For example, an implant may release the drug at a rate effective to sustain a therapeutically effective amount of drug for about one month after being placed in an eye. As another example, the implant may release drug at a rate effective to sustain a therapeutically effective amount of drug for more than forty days, such as for about six months.

Examples of the implant formulation of the invention are drug 30%, R208 35% and RG755S 35%; drug 30%, R208 35% and RG752S 35%; drug 30%, R208 35% and R203S 35%; and drug 30%, R203S 35% and RG755S 35%.

The range of concentrations of the polymer components that can be used in the implant formulation are 10 to 60%, R208; 10 to 60%, R203S; 10 to 60%, RG752S, and 10 to 60%, 755S. The drug may comprise (w/w) from 10 to 60%, more preferably from 20 to 50%, e.g. 30%, of the implant.

The amounts given above are in weight/weight percent.

PLA/PLGA polymers from the Resomer product line are available from Evonik Industries AG, Germany, and include the following:

| Resomer | Monomer ratio | i.v. dL/g |
| --- | --- | --- |
| RG502 | 50:50 poly (D,L-lactide-co-glycolide) | 0.2 |
| RG502H | 50:50 poly (D,L-lactide-co-glycolide), acid end | 0.2 |
| RG503 | 50:50 poly (D,L-lactide-co-glycolide) | 0.3 |
| RG504 | 50:50 poly (D,L-lactide-co-glycolide) | 0.5 |
| RG505 | 50:50 poly (D,L-lactide-co-glycolide) | 0.7 |

-continued

| Resomer | Monomer ratio | i.v. dL/g |
| --- | --- | --- |
| RG506 | 50:50 poly (D,L-lactide-co-glycolide) | 0.8 |
| RG752 | 75:25 poly (D,L lactide-co-glycolide) | 0.2 |
| RG755 | 75:25 poly(D,L lactide-co-glycolide) | 0.6 |
| RG756 | 75:25 poly(D,L lactide-co-glycolide) | 0.8 |
| RG858 | 85:15 poly (D,L-lactide-co-glycolide) | 1.5 |
| R202H | poly (D,L-lactide), acid end | 0.2 |
| R203S | poly (D,L-lactide) | 0.3 |
| R206 | poly (D,L-lactide) | 0.6 |
| R104 | poly (D,L-lactide) | (3500) |

The solvent used to make the thin clear film of the invention is selected for its ability to dissolve sufficient polymer and latanoprost to provide solutions which may be cast and evaporated to form a thin flexible film of latanoprost surrounded by a matrix of said polymer.

Useful solvents include dichloromethane, ethyl acetate, chloroform, acetone, acetonitrile, etc. For solvating properties and ease of solvent removal acetone or dichloromethane, e.g. dichloromethane, is preferred.

The solution may comprise from 10 to 75% solids, e.g. 30 to 50%, wherein said solids comprise latanoprost, polymer and other components which are useful for modifying the release of latanoprost from the resulting film and/or plasticizers of said polymer which contribute to the flexibility of the film.

The following examples are intended to illustrate the present invention.

Example 1

The film-shaped implant of the invention is made by solvent casting and contains 30% latanoprost, 0-70% of a biodegradable poly (D,L-lactide-co-glycolide) polymer (Resomer® RG755S or Resomer® RG752S) and 0-70% of a biodegradable poly (D,L-lactide) polymer (Resomer® R208 or Resomer® R203S). The formulations and drug release profiles for the invention are summarized in Table 1 and FIG. 1, respectively.

Polymers were used as received from Boehringer Ingelheim (Resomer®) and latanoprost was used as received from Daiichi Fine Chemical Co., Ltd.

The film-shaped implants of this example are made by solvent casting. The implants are circular-shaped, but they can be made into any geometric shape by changing the cutting-punch.

Lantanoprost and the polymer were initially mixed using a spatula in a weigh-boat for 3 minutes. The samples were then transferred into glass culture dish (60×15-mm) and dissolved in 10-ml dichloromethane, Chromasolv Plus for HPLC 99.9%. The solutions were cast in the dishes and dried in a fume hood for 24 hours.

The dried film was cut using 4-mm biopsy punch (approximately 2.0-mg), and was placed into a 10-mL vial containing 0.01M phosphate buffered saline (pH 7.4)+0.1% Triton X100. The samples were then transferred into a shaking water bath set at 37° C. and 50 rpm. At various time-points, the solution was removed and analyzed by HPLC for the amount of released latanoprost. The removed solution is replaced with fresh phosphate buffered saline solution.

TABLE 1

| | Latanoprost Containing Film Formulations w/w, % | | | |
|---|---|---|---|---|
| Latanoprost | Resomer R208 | Resomer R203S | Resomer RG752S | Resomer RG755S |
| 30 | 35 | 0 | 0 | 35 |
| 30 | 35 | 0 | 35 | 0 |
| 30 | 35 | 35 | 0 | 0 |
| 30 | 0 | 35 | 0 | 35 |

Figure 1B:
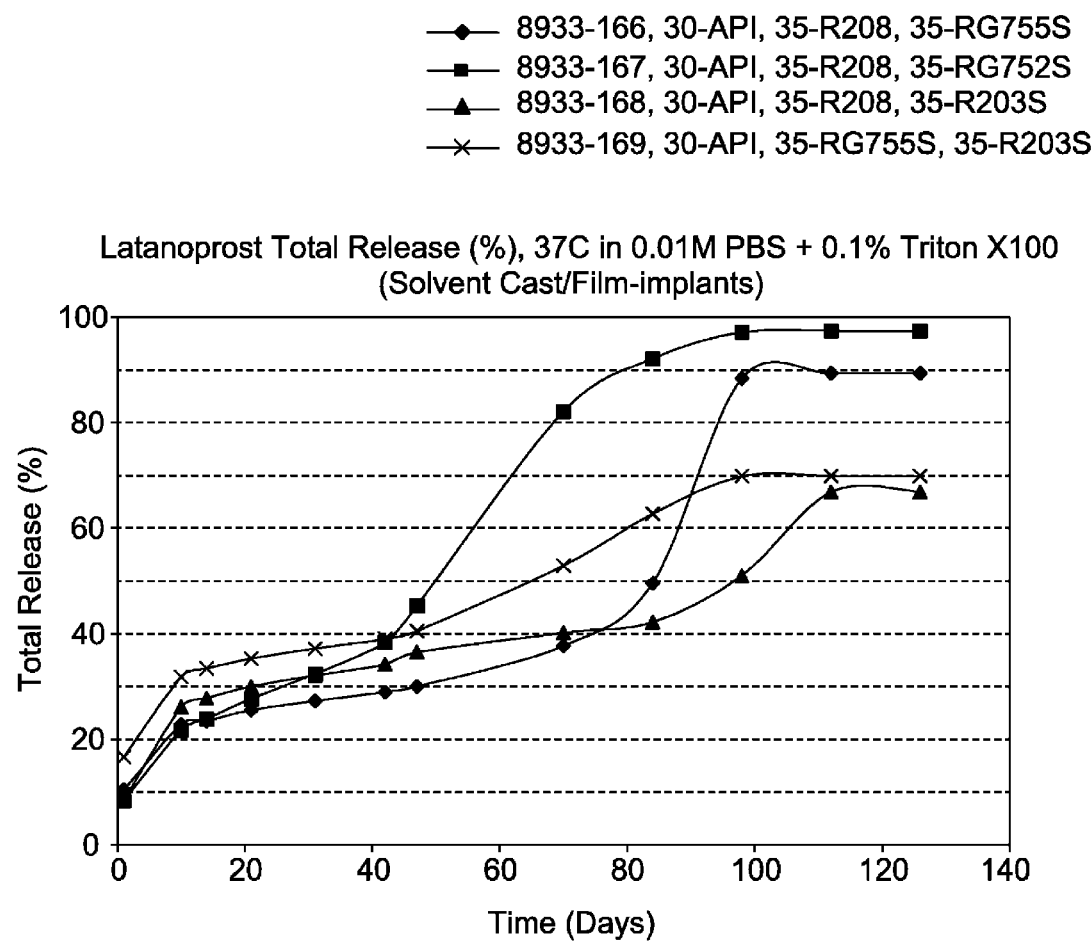

Drug release profiles are shown in FIGS. 1A and B.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims

What is claimed is:

1. A biodegradable implant for reducing intraocular pressure in an eye of an individual in need thereof, the implant consisting of about 30% by weight latanoprost, about 35% by weight R208, which is an ester terminated poly(D,L-lactide) having an inherent viscosity of about 1.8-2.2 dl/g, and about 35% by weight RG755, which is an ester terminated poly(D,L-lactide-co-glycolide) having an inherent viscosity of about 0.50-0.70 dl/g and a D,L-lactide:glycolide ratio of about 75:25, wherein the implant is in the form of a rolled film that, once inserted into an eye, can unfurl to its original shape to thereby expose its entire surface to provide for drug diffusion out of the film into the eye, and wherein the implant releases latanoprost continuously for at least 30 days after placement in the eye of the individual.

2. A biodegradable implant for reducing intraocular pressure in an eye of an individual in need thereof, the implant consisting of about 30% by weight latanoprost, about 35% by weight R208, which is an ester terminated poly(D,L-lactide) having an inherent viscosity of about 1.8-2.2 dl/g, and about 35% by weight R203S, which is an ester terminated poly(D,L-lactide) having an inherent viscosity of about 0.25-0.35 dl/g, wherein the implant is in the form of a rolled film that, once inserted into an eye, can unfurl to its original shape to thereby expose its entire surface to provide for drug diffusion out of the film into the eye, and wherein the implant releases latanoprost continuously for at least 30 days after placement in the eye of the individual.

3. A method for making a biodegradable intraocular implant according to claim 1 or 2, the method comprising:
   a) combining latanoprost and the biodegradable polymers in a receptacle;
   b) mixing the latanoprost and biodegradable polymers in the receptacle using a spatula to form a mixture;
   c) transferring the mixture to a glass culture dish;
   d) dissolving the dish mixture in a solvent selected from the group consisting of dichloromethane, ethyl acetate, chloroform, acetone, and acetonitrile, to form a solution;
   e) casting the solution into a dish;
   f) drying the cast for about 24 hours to form a film;
   g) cutting the film into circular portions of about 4 mm in diameter;
   h) rolling said circular portions to form a rolled film for placement in the eye of an individual in need thereof, wherein the rolled film, once inserted into an eye, can unfurl to its original shape to thereby expose its entire surface to provide for drug diffusion out of the film into the eye.

4. A biodegradable implant according to claim 1 or 2, wherein said film is about 100 μm to about 500 μm thick and about 2 mm to about 6 mm in diameter.

* * * * *

UNITED STATES PATENT AND TRADEMARK OFFICE
CERTIFICATE OF CORRECTION

PATENT NO. : 8,715,713 B2
APPLICATION NO. : 13/457785
DATED : May 6, 2014
INVENTOR(S) : Alazar N. Ghebremeskel et al.

It is certified that error appears in the above-identified patent and that said Letters Patent is hereby corrected as shown below:

In the Specification:

In column 4, line 5, delete "dish:" and insert -- dish; --, therefor.

In column 8, line 53, delete "Lantanoprost" and insert -- Latanoprost --, therefor.

In column 9, line 20, after "claims" insert -- . --.

Signed and Sealed this
Fifteenth Day of July, 2014

Michelle K. Lee
*Deputy Director of the United States Patent and Trademark Office*